US00PP17632P2

(12) United States Plant Patent
Olesen et al.

(10) Patent No.: US PP17,632 P2
(45) Date of Patent: Apr. 24, 2007

(54) COMPACT FLORIBUNDA ROSE PLANT 'POULAC006'

(50) Latin Name: ***Rosa* hybrid**
Varietal Denomination: POUlac006

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 376 days.

(21) Appl. No.: 10/342,702

(22) Filed: Jan. 14, 2003

(51) Int. Cl.
*A01H 5/00* (2006.01)

(52) U.S. Cl. ..... Plt./150
(58) Field of Classification Search ..... Plt./150
See application file for complete search history.

(56) References Cited

U.S. PATENT DOCUMENTS

PP9,687 P * 11/1996 Olesen et al. ..... Plt./122
PP11,501 P * 9/2000 Olesen et al. ..... Plt./147
PP11,598 P * 10/2000 Olesen et al. ..... Plt./143
PP12,557 P2 * 4/2002 Olesen et al. ..... Plt./149

OTHER PUBLICATIONS

UPOV ROM GTITM Computer Database, GTI JOUVE Retrieval Software 2003/01 citation(s) for 'POULsail', poulac006.* http://www.helpmefind.com/rose/pl.php?n=35691.* https://www.arenaroses.com/ama/cgi–bin/dc.pl?nd=full&key=VEPABR.*

* cited by examiner

*Primary Examiner*—Kent Bell
*Assistant Examiner*—W. C. Haas

(57) ABSTRACT

A new compact floribunda rose plant which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa* hybrid.
Variety denomination: 'POULac006'.

SUMMARY OF THE INVENTION

The present invention constitutes a new and distinct variety of compact floribunda rose plant which originated from a controlled crossing between the seed parent, an unnamed seedling, not patented, and 'POULrouge' described and illustrated in U.S. Plant Pat. No. 9,687. The two parents were crossed and the resulting seeds were planted in a controlled environment. The new variety is named 'POULac006'.

The new variety may be distinguished from its pollen parent by the following combination of characteristics:

1. 'POULrouge' has a petal count of 30 to 35 petals, while that of 'POULac006' is 35 to 40.
2. 'POULrouge' has an upper-surface petal color of Red Group 40B, while that of 'POULac006' is Red Group 40A.
3. 'POULrouge' has a bloom diameter of 38 mm, while that of 'POULac006' is 60 mm.

The new variety may be distinguished from the seed parent, mainly by flower color. The seed parent has dark red flowers, while 'POULac006' has orange red flowers.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULac006' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULac006' was selected by the inventors as a single plant from the progeny of the hybridization in April of 1994.

Asexual reproduction of 'POULac006' by cuttings and traditional budding was first done by L. Pernille and Mogens N. Olesen in their nursery in Fredensborg, Denmark in June of 1994. This initial and other subsequent propagations conducted in controlled environments have demonstrated that the characteristics of 'POULac006' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULac006'. Specifically illustrated in the drawing:

1 Stem showing branching and the attachment of leaves, buds, and peduncles;

2. Flower bud, partially opened bud, and open bloom;

3. Flower petals, detached;

4. Sepals, receptacle, and pedicel;

5. Stem as well as a bare stem exhibiting thorns;

6. Leaves.

DETAILED DESCRIPTION OF THE VARIETY

The following is a description of 'POULac006', as observed in its growth in a field nursery in Jackson County, Oreg. Observed plants are 2 years of age, and were cultivated on *Rosa multiflora* understock. Color references are made using The Royal Horticultural Society (London, England) Colour Chart, 1995, except where common terms of color are used.

For a comparison, several physical characteristics of the rose variety 'Poulsail', a rose variety from the same inventors described and illustrated in U.S. Plant Pat. No. 11,501 issued on Sep. 5, 2000, are compared to 'POULac006' in Chart 1.

CHART 1

| Characteristic | 'Poulac006' | 'Poulsail' |
|---|---|---|
| Average Leaf Length | 110 mm | 90 mm |
| Average Leaf Width | 83 mm | 61 mm |
| Average Terminal Leaflet Length | 51 mm | 40 mm |
| Average Terminal Leaflet width | 31 mm | 25 mm |
| General Tonality of Flower Color | 40A | 40C |

Parents: 'POULrouge'×an unnamed seedling.

FLOWER AND FLOWER BUD

Blooming habit: Recurrent.

Flower bud:

*Size.*—Upon opening, 20 to 24 mm in length from base of receptacle to end of bud. Bud diameter is typically 13 to 15 mm.

*Bud form.*—Pointed ovoid.

*Bud color.*—As sepals unfold, Orange-Red Group Red Group 42A. At ¼ opening, Red Group 42A.

*Sepals.*—Upper surface is Yellow-Green Group 144B, with areas of Yellow-Green Group 144A. Lower surface is Yellow-Green Group 144A, with anthocyanin intonations of Greyed-Orange Group 176A. Moderately strong foliaceous appendages on three of the five sepals. Surfaces of sepals are moderately pubescent. Stipitate glands are present on sepal edges and undersides. Shape: Sepal apex is cirrhose. Base is flat at union with peduncle. Size: 25 mm long×8 mm wide.

*Receptacle.*—Surface: Smooth and glossy. Shape: Funnel-shaped. Size: 5 mm (h)×6 mm (w). Color: Yellow-Green Group 144B.

*Peduncle.*—Surface: With fragrant stipitates. Length: 35 to 45 mm average length. Color: Yellow-Green Group 144B. On plants grown under high light conditions, peduncle may exhibit intonations of Greyed-Red Group 181A. Strength: Strong.

*Borne.*—3 to 5 buds per stem.

*Anthocyanin.*—Peduncles are mottled with Greyed-Red Group 181A.

Flower bloom:

*Fragrance.*—None.

*Duration.*—As a pot plant, flowers last from 8 to 10 days.

*Size.*—Average flower diameter is 60 to 80 mm when open.

*Form.*—

*Shape of flower when viewed from the side.*—Upon opening, upper part: Convex. Upon opening, lower part: Concave. Open flower, upper part: Convex. Open flower, lower part: Concave.

*Petalage.*—Average range: 35 to 40 petals under normal conditions with 5 to 10 petaloids.

Color:

*Upon opening, petals.*—Outermost petals: Outer Side: Red Group 43C. Inner Side: Red Group 40A. Innermost petals: Outer Side: Red Group 43C. Inner Side: Red Group 40A.

*Upon opening, basal petal spots.*—Outermost petals: Outer Side: Yellow Group 12B. Inner Side: Yellow Group 12B. Innermost petals: Outer Side: Yellow Group 12B. Inner Side: Yellow Group 12B.

*After opening, petals.*—Outermost petals: Outer Side: Red Group 43C. Inner Side: Red Group 40A. Innermost petals: Outer Side: Red Group 43C. Inner Side: Red Group 40A.

*After opening, basal petal spots.*—Outermost petals: Outer Side: Yellow Group 12B. Inner Side: Yellow Group 12B. Innermost petals: Outer Side: Yellow Group 12B. Inner Side: Yellow Group 12B.

General tonality: On open flower, Red Group 40A. No change in the general tonality at the end of the $7^{th}$ day. Afterwards, general tonality is Red Group 40B and C.

Petals:

*Petal reflex.*—Moderate.

*Petal margin.*—Entire.

*Petal texture.*—Smooth.

*Shape.*—Obovate.

*Size.*—Outer petals are typically 30 to 33 mm in length by 30 to 33 mm wide.

*Petaloids.*—Quantity: 5 to 6. Size: 20 mm long; 10 mm wide. Color: Upper surface is Red Group 40A, lower surface is Red Group 43C.

*Thickness.*—Thin.

*Arrangement.*—Not formal.

Reproductive organs:

*Pistils.*—Length: 12 mm long. Quantity: 20 to 25.

*Pollen.*—Color: Yellow-Orange Group 14C. Quantity: Scant.

*Anthers.*—Size: 2 to 3 mm long. Color: Greyed-White Group 156D. Quantity: 30 to 35.

*Filaments.*—Color: Greyed-Red Group 181C. Length: 2 mm.

*Stigmas.*—Slightly superior in location to anthers. Color: Yellow-Green Group 145D.

*Styles.*—Color: Yellow-Green Group 145D.

*Seed formation.*—No hips observed.

PLANT

Plant growth: Vigorous, compact and bushy. When grown as a nursery plant on its own roots the average plant height is 40 to 60 cm and the average plant width is 50 cm.

Stems:

*Color.*—Young wood: Yellow-Green Group 144A. Older wood: Yellow-Green Group 144A.

*Prickles.*—Incidence: 10 thorns per 10 cm of stem. Size: Average length: 8 mm. Color: Greyed-Red Group 182A. Shape: Curved.

*Surface.*—Young wood: Rough. Older wood: Rough.

Plant foliage: Normal number of leaflets on normal leaves in middle of the stem: 5 leaflets.

*Leaf size.*—On average, compound leaves are 110 mm (l)×83 mm (w).

*Quantity.*—2 leaves per 10 cm of stem.

*Internodes.*—Normally, 40 to 50 mm between nodes.

*Color.*—Upper Leaf Surface: Green Group 137A. Lower Leaf Surface: Green Group 137C. Juvenile foliage: Upper Leaf Surface: Green Group 137A. Lower Leaf Surface: Green Group 137C.

Plant leaves and leaflets:

*Stipules.*—Size: 10 to 15 mm long. Color: Yellow-Green Group 144C. Presence of stipitate glands: On stipule edges.

*Petiole.*—Length: 25 mm long. Color: Green Group 137A. Underneath: Yellow-Green Group 144A, with single, small thorn. Margins: Green Group 137A.

*Rachis.*—Color: Green Group 137A. Underneath: Yellow-Green Group 144A, with single, small thorn. Margins: Green Group 137A.

*Leaflet.*—Size: Terminal leaflets are normally 50 to 52 mm long by 30 to 32 mm wide. Edge: Serrated. Shape: Base is rounded, while apex is acute. Texture: Thin: Glossiness: Moderate. Arrangement: Odd pinnate. Venation: Reticulate. Nearest color reference is Yellow-Green Group 151 A.

Disease resistance: Average resistance to mildew, black spot, and *Botrytis* under normal growing conditions in Jackson County, Oreg.

Cold hardiness: 'POULac006' has been found to be resistant to damage from cold, heat and drought in USDA Zone 7.

It is claimed:

1. A new and distinct variety of rose plant of the compact floribunda class, substantially as herein illustrated and described as a distinct and novel rose variety due to its abundant, red flowers, vigorous growth, compact habit, suitability for production from softwood cuttings in pots, and durable flowers and foliage which make the variety suitable for distribution in the floral industry.

* * * * *

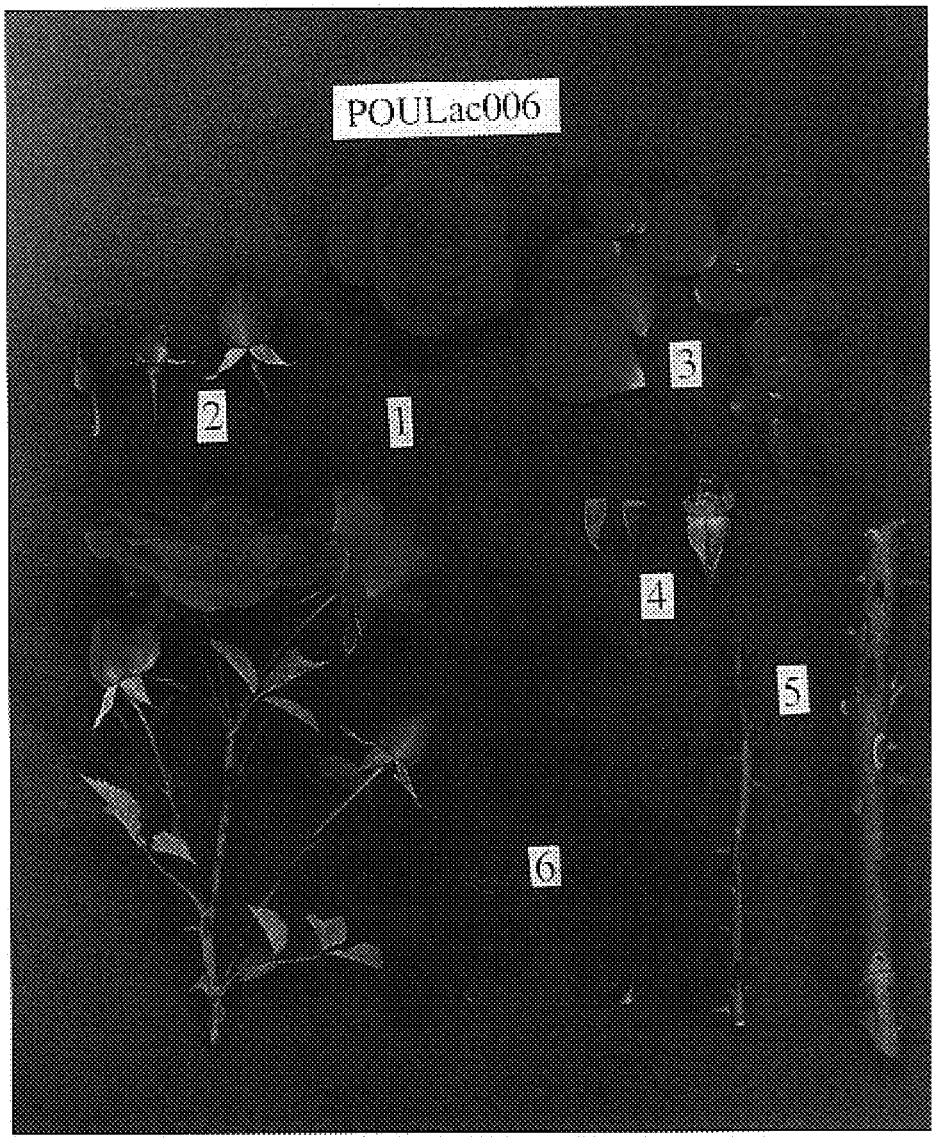
POULac006
1
2
3
4
5
6